(12) United States Patent
Nuttall

(10) Patent No.: US 8,082,873 B2
(45) Date of Patent: Dec. 27, 2011

(54) DRIVE MECHANISM FOR AN INDICATING DEVICE

(75) Inventor: Michael Nuttall, London (CA)

(73) Assignee: Trudell Medical International, London (CA)

( * ) Notice: Subject to any disclaimer, the term of this patent is extended or adjusted under 35 U.S.C. 154(b) by 250 days.

(21) Appl. No.: 12/434,917

(22) Filed: May 4, 2009

(65) Prior Publication Data

US 2009/0272312 A1 Nov. 5, 2009

Related U.S. Application Data

(60) Provisional application No. 61/126,436, filed on May 5, 2008.

(51) Int. Cl.
*A61M 15/00* (2006.01)
*B67D 7/22* (2010.01)

(52) U.S. Cl. .................. 116/285; 116/307; 128/205.23; 222/36

(58) Field of Classification Search ............. 128/200.23, 128/205.23; 222/23, 36, 38; 116/284, 285, 116/296–300, 305–307, 309, 311, 312, 315–318, 116/334, 335, 337, DIG. 1
See application file for complete search history.

(56) References Cited

U.S. PATENT DOCUMENTS

| | | | |
|---|---|---|---|
| 165,054 A | 6/1875 | Baldwin | |
| 498,851 A | 6/1893 | Jones | |
| 1,219,858 A | 3/1917 | Patterson | |
| 2,455,962 A | 12/1948 | Wheeler et al. | |
| 2,580,292 A | 12/1951 | Geary et al. | |
| 2,587,147 A | 2/1952 | Guion et al. | |
| 2,630,027 A | 3/1953 | Wunderlich | |
| 2,644,452 A | 7/1953 | Brown | |
| 2,767,680 A | 10/1956 | Lermer | |
| 2,770,711 A | 11/1956 | Baranowski | |
| 2,841,190 A | 7/1958 | Sheck | |
| 2,883,086 A | 4/1959 | Davison et al. | |
| 2,939,597 A | 6/1960 | Greene | |
| 2,943,730 A | 7/1960 | Tregilgas | |
| 2,953,242 A | 9/1960 | Shaw | |

(Continued)

FOREIGN PATENT DOCUMENTS

AU 598250 B2 6/1990

(Continued)

OTHER PUBLICATIONS

International Search Report in International Application No. PCT/IB2005/002764, dated Feb. 21, 2006, 8 pages.

(Continued)

*Primary Examiner* — Amy Cohen Johnson
(74) *Attorney, Agent, or Firm* — Brinks Hofer Gilson & Lione

(57) ABSTRACT

An indicating device includes a drive member and a driven member. The driven member is non-rotatably immobilized by the successive engagement of a convex surface on the drive member with a plurality of concave surfaces on the driven member. The driven member further includes a plurality of protrusions that are successively received in a recess of the drive member as an engagement member engages the driven member and rotates the driven member. The driven member has dispensing indicia. In another aspect, an indicating device includes an indicator member having dispensing indicia. A stop member is selectively engaged with successive ones of a plurality of stop surfaces on the indicator member such that the indicator member is non-rotatable. Methods for indicating the amount of substance that have been dispensed from or remain in a container are also provided.

19 Claims, 4 Drawing Sheets

U.S. PATENT DOCUMENTS

| | | |
|---|---|---|
| 3,001,524 A | 9/1961 | Maison et al. |
| 3,073,468 A | 1/1963 | Arneson |
| 3,085,745 A | 4/1963 | Auberger |
| 3,119,557 A | 1/1964 | Chapman |
| 3,120,318 A | 2/1964 | Rigor |
| 3,148,801 A | 9/1964 | Radeloff et al. |
| 3,151,599 A | 10/1964 | Livingston |
| 3,170,597 A | 2/1965 | Reichenberger |
| 3,187,963 A | 6/1965 | Anderson |
| 3,189,232 A | 6/1965 | Joffe |
| 3,191,867 A | 6/1965 | Helms |
| 3,240,389 A | 3/1966 | Genua |
| 3,334,731 A | 8/1967 | Dale |
| 3,344,951 A | 10/1967 | Gervais |
| 3,361,306 A | 1/1968 | Grim |
| 3,402,863 A | 9/1968 | Green |
| 3,419,187 A | 12/1968 | Bazarnic |
| 3,446,179 A | 5/1969 | Bender |
| 3,477,561 A | 11/1969 | Espinal |
| 3,495,567 A | 2/1970 | Hayes et al. |
| 3,511,409 A | 5/1970 | Huck |
| 3,549,057 A | 12/1970 | Perez |
| 3,568,629 A | 3/1971 | Porter |
| 3,572,282 A | 3/1971 | Trump et al. |
| 3,589,563 A | 6/1971 | Carragan et al. |
| 3,612,349 A | 10/1971 | Thomas |
| 3,654,890 A | 4/1972 | Rigney et al. |
| 3,655,952 A | 4/1972 | Johnson et al. |
| 3,688,945 A | 9/1972 | Harman, Jr. et al. |
| 3,753,417 A | 8/1973 | Garby |
| 3,766,882 A | 10/1973 | Babbitt, III |
| 3,789,843 A | 2/1974 | Armstrong et al. |
| 3,792,242 A | 2/1974 | Hanson |
| 3,796,348 A | 3/1974 | Zipper |
| 3,797,748 A | 3/1974 | Nozawa et al. |
| 3,802,608 A | 4/1974 | Gullett |
| 3,831,808 A | 8/1974 | Bender |
| 3,831,812 A | 8/1974 | Dolan |
| 3,845,883 A | 11/1974 | Johnson et al. |
| 3,848,774 A | 11/1974 | Schimke |
| 3,886,879 A | 6/1975 | Frost et al. |
| 3,887,099 A | 6/1975 | Gillman et al. |
| 3,921,568 A | 11/1975 | Fish |
| 3,926,326 A | 12/1975 | Grau |
| 3,950,939 A | 4/1976 | Meisner |
| 3,960,713 A | 6/1976 | Carey |
| 3,977,554 A | 8/1976 | Costa |
| 3,994,421 A | 11/1976 | Hansen |
| 4,011,829 A | 3/1977 | Wachsmann et al. |
| 4,029,033 A | 6/1977 | Kerwin et al. |
| 4,034,757 A | 7/1977 | Glover |
| 4,037,719 A | 7/1977 | Perlmutter |
| 4,069,935 A | 1/1978 | Hampel |
| 4,069,942 A | 1/1978 | Marshall et al. |
| 4,074,831 A | 2/1978 | Roach |
| 4,078,661 A | 3/1978 | Thomas |
| 4,094,408 A | 6/1978 | Ford |
| 4,162,746 A | 7/1979 | Anderson et al. |
| 4,164,301 A | 8/1979 | Thayer |
| 4,188,984 A | 2/1980 | Lyall |
| 4,220,247 A | 9/1980 | Kramer |
| 4,291,688 A | 9/1981 | Kistler |
| 4,300,548 A | 11/1981 | Jones |
| 4,319,128 A | 3/1982 | Dow, Jr. et al. |
| 4,345,541 A | 8/1982 | Villa-Real |
| 4,347,804 A | 9/1982 | Villa-Real |
| 4,347,853 A | 9/1982 | Gereg et al. |
| 4,350,265 A | 9/1982 | Griffiths et al. |
| 4,354,621 A | 10/1982 | Knickerbocker |
| 4,357,192 A | 11/1982 | Moser |
| 4,365,722 A | 12/1982 | Kramer |
| 4,368,381 A | 1/1983 | Ishiyama |
| 4,405,045 A | 9/1983 | Villa-Real |
| 4,419,016 A | 12/1983 | Zoltan |
| 4,432,300 A | 2/1984 | Lyss |
| 4,436,223 A | 3/1984 | Wilson |
| 4,440,306 A | 4/1984 | Van Buskirk et al. |
| 4,489,834 A | 12/1984 | Thackrey |
| 4,500,005 A | 2/1985 | Forrester |
| 4,501,370 A | 2/1985 | Kelley |
| 4,511,150 A | 4/1985 | Seguenot |
| 4,523,933 A | 6/1985 | Laush et al. |
| 4,528,933 A | 7/1985 | Allen |
| 4,534,345 A | 8/1985 | Wetterlin |
| 4,538,744 A | 9/1985 | Weissenborn |
| 4,548,157 A | 10/1985 | Hevoyan |
| 4,562,933 A | 1/1986 | Dennis |
| 4,565,302 A | 1/1986 | Pfeiffer et al. |
| 4,599,508 A | 7/1986 | Smetaniuk |
| 4,634,012 A | 1/1987 | Kelley |
| 4,637,528 A | 1/1987 | Wachinski et al. |
| 4,641,759 A | 2/1987 | Kelley |
| 4,646,936 A | 3/1987 | Frazier et al. |
| 4,662,520 A | 5/1987 | Griffin |
| 4,664,107 A | 5/1987 | Wass |
| 4,666,051 A | 5/1987 | Trick |
| 4,668,218 A | 5/1987 | Virtanen |
| 4,677,975 A | 7/1987 | Edgar et al. |
| 4,693,399 A | 9/1987 | Hickman et al. |
| 4,705,182 A | 11/1987 | Newel-Lewis |
| 4,722,729 A | 2/1988 | Dettbarn et al. |
| 4,723,673 A | 2/1988 | Tartaglia et al. |
| 4,727,886 A | 3/1988 | Conrardy et al. |
| 4,736,871 A | 4/1988 | Luciani et al. |
| 4,749,093 A | 6/1988 | Trick |
| 4,753,189 A | 6/1988 | Mastman et al. |
| 4,756,423 A | 7/1988 | Holtsch |
| 4,782,966 A | 11/1988 | Thackrey |
| 4,792,664 A | 12/1988 | Schwab |
| 4,817,822 A | 4/1989 | Rand et al. |
| 4,890,572 A | 1/1990 | Huang |
| 4,934,358 A | 6/1990 | Nilsson et al. |
| 4,934,568 A | 6/1990 | Fuchs |
| 4,947,875 A | 8/1990 | Brooks et al. |
| 4,955,371 A | 9/1990 | Zamba et al. |
| 4,969,578 A | 11/1990 | Gander et al. |
| 4,973,250 A | 11/1990 | Milman |
| 4,984,158 A | 1/1991 | Hillsman |
| 5,009,338 A | 4/1991 | Barker |
| 5,011,032 A | 4/1991 | Rollman |
| 5,020,527 A | 6/1991 | Dessertine |
| 5,027,806 A | 7/1991 | Zoltan et al. |
| 5,027,808 A | 7/1991 | Rich et al. |
| 5,038,972 A | 8/1991 | Muderlak et al. |
| 5,060,643 A | 10/1991 | Rich et al. |
| 5,069,204 A | 12/1991 | Smith et al. |
| 5,082,129 A | 1/1992 | Kramer |
| 5,082,130 A | 1/1992 | Weinstein |
| 5,115,929 A | 5/1992 | Buono |
| 5,174,473 A | 12/1992 | Marelli |
| 5,184,761 A | 2/1993 | Lee |
| 5,188,251 A | 2/1993 | Kusz |
| 5,190,643 A | 3/1993 | Duncan et al. |
| 5,209,375 A | 5/1993 | Fuchs |
| 5,215,079 A | 6/1993 | Fine et al. |
| 5,217,004 A | 6/1993 | Blasnik et al. |
| 5,224,474 A | 7/1993 | Bloomfield |
| 5,227,764 A | 7/1993 | Umemoto |
| 5,228,586 A | 7/1993 | Fuchs |
| 5,242,067 A | 9/1993 | Garby et al. |
| 5,243,970 A | 9/1993 | Amrosio et al. |
| 5,261,548 A | 11/1993 | Barker et al. |
| 5,263,475 A | 11/1993 | Altermatt et al. |
| 5,284,133 A | 2/1994 | Burns et al. |
| 5,289,946 A | 3/1994 | Fuchs |
| 5,299,701 A | 4/1994 | Barker et al. |
| 5,300,042 A | 4/1994 | Kossoff et al. |
| 5,301,873 A | 4/1994 | Burke et al. |
| 5,328,597 A | 7/1994 | Boldt, Jr. et al. |
| 5,331,953 A | 7/1994 | Andersson et al. |
| 5,335,823 A | 8/1994 | Fuchs et al. |
| 5,349,944 A | 9/1994 | Chippendale et al. |
| 5,349,945 A | 9/1994 | Wass et al. |
| 5,356,012 A | 10/1994 | Tang et al. |
| 5,363,842 A | 11/1994 | Mishelevich et al. |
| 5,370,267 A | 12/1994 | Schroeder |
| 5,382,243 A | 1/1995 | Mulholland |

| | | |
|---|---|---|
| RE34,847 E | 2/1995 | Muderlak et al. |
| 5,388,572 A | 2/1995 | Mulhauser et al. |
| 5,392,768 A | 2/1995 | Johansson et al. |
| 5,394,866 A | 3/1995 | Ritson et al. |
| 5,397,028 A | 3/1995 | Jesadanont |
| 5,411,173 A | 5/1995 | Weinstein |
| 5,421,482 A | 6/1995 | Garby et al. |
| 5,437,270 A | 8/1995 | Braithwaite |
| 5,447,150 A | 9/1995 | Bacon |
| 5,448,042 A | 9/1995 | Robinson et al. |
| 5,482,030 A | 1/1996 | Klein |
| 5,482,163 A | 1/1996 | Hoffman |
| 5,505,192 A | 4/1996 | Samiotes et al. |
| 5,505,195 A | 4/1996 | Wolf et al. |
| 5,509,905 A | 4/1996 | Michel |
| 5,519,197 A | 5/1996 | Robinson et al. |
| 5,520,166 A | 5/1996 | Ritson et al. |
| 5,522,378 A | 6/1996 | Ritson et al. |
| 5,544,647 A | 8/1996 | Jewett et al. |
| 5,549,101 A | 8/1996 | Trofast et al. |
| 5,564,414 A | 10/1996 | Walker et al. |
| 5,574,268 A | 11/1996 | Herman et al. |
| 5,611,444 A | 3/1997 | Garby et al. |
| 5,617,844 A | 4/1997 | King |
| 5,622,163 A | 4/1997 | Jewett et al. |
| 5,625,334 A | 4/1997 | Compton |
| 5,625,659 A | 4/1997 | Sears |
| 5,638,970 A | 6/1997 | Garby et al. |
| 5,657,748 A | 8/1997 | Braithwaite |
| 5,676,129 A | 10/1997 | Rocci, Jr. et al. |
| 5,687,710 A | 11/1997 | Ambrosio et al. |
| 5,692,492 A | 12/1997 | Bruna et al. |
| 5,694,882 A | 12/1997 | Marshall |
| 5,718,355 A | 2/1998 | Garby et al. |
| 5,724,957 A | 3/1998 | Rubsamen et al. |
| 5,732,836 A | 3/1998 | Barker et al. |
| 5,740,792 A | 4/1998 | Ashley et al. |
| 5,758,638 A | 6/1998 | Kreamer |
| 5,772,074 A | 6/1998 | Dial et al. |
| 5,794,612 A | 8/1998 | Wachter et al. |
| 5,799,651 A | 9/1998 | Garby et al. |
| 5,803,283 A | 9/1998 | Barker et al. |
| 5,809,997 A | 9/1998 | Wolf |
| 5,826,571 A | 10/1998 | Casper et al. |
| 5,829,434 A | 11/1998 | Ambrosio et al. |
| 5,845,777 A | 12/1998 | Najmi |
| 5,852,590 A | 12/1998 | De La Huerga |
| 5,871,007 A | 2/1999 | Clark, Jr. |
| 5,873,995 A | 2/1999 | Huang et al. |
| 5,882,507 A | 3/1999 | Tanner et al. |
| 5,896,855 A | 4/1999 | Hobbs |
| 5,896,990 A | 4/1999 | Barzana |
| 5,899,201 A | 5/1999 | Schultz et al. |
| 5,904,139 A | 5/1999 | Hauser |
| 5,957,896 A | 9/1999 | Bendek et al. |
| 5,988,496 A | 11/1999 | Bruna |
| 6,000,159 A | 12/1999 | Hornung |
| 6,012,450 A | 1/2000 | Rubsamen |
| 6,029,659 A | 2/2000 | O'Connor |
| 6,059,133 A | 5/2000 | Lai |
| 6,062,214 A | 5/2000 | Howlett |
| 6,076,521 A | 6/2000 | Lindahl et al. |
| 6,082,358 A | 7/2000 | Scarrott et al. |
| 6,089,180 A | 7/2000 | Nichols, Jr. |
| 6,119,684 A | 9/2000 | Nohl et al. |
| 6,138,669 A | 10/2000 | Rocci, Jr. et al. |
| 6,142,339 A | 11/2000 | Blacker et al. |
| 6,148,815 A | 11/2000 | Wolf |
| 6,149,054 A | 11/2000 | Cirrillo |
| 6,155,251 A | 12/2000 | Hauser |
| 6,161,724 A | 12/2000 | Blacker et al. |
| 6,164,494 A | 12/2000 | Marelli |
| 6,183,087 B1 | 2/2001 | Kirkpatrick et al. |
| 6,202,642 B1 | 3/2001 | McKinnon et al. |
| 6,223,744 B1 | 5/2001 | Garon |
| 6,234,168 B1 | 5/2001 | Bruna |
| 6,283,365 B1 | 9/2001 | Bason |
| 6,328,037 B1 | 12/2001 | Scarrott et al. |
| 6,336,453 B1 | 1/2002 | Scarrott et al. |
| 6,360,739 B1 | 3/2002 | Rand et al. |
| 6,405,727 B1 | 6/2002 | MacMichael et al. |
| 6,415,785 B1 | 7/2002 | Stage |
| 6,425,392 B1 | 7/2002 | Sosiak |
| 6,431,168 B1 | 8/2002 | Rand et al. |
| 6,435,372 B1 | 8/2002 | Blacker et al. |
| 6,446,627 B1 | 9/2002 | Bowman et al. |
| 6,474,331 B1 | 11/2002 | Rand et al. |
| 6,481,438 B1 | 11/2002 | Gallem et al. |
| 6,484,717 B1 | 11/2002 | Dagsland et al. |
| 6,516,799 B1 | 2/2003 | Greenwood et al. |
| 6,529,446 B1 | 3/2003 | De La Huerga |
| 6,561,384 B2 | 5/2003 | Blacker et al. |
| 6,601,582 B2 | 8/2003 | Rand et al. |
| 6,615,827 B2 | 9/2003 | Greenwood et al. |
| 6,659,307 B1 | 12/2003 | Stradella |
| 6,679,251 B1 | 1/2004 | Gallem et al. |
| 6,701,917 B2 | 3/2004 | O'Leary |
| 6,718,972 B2 | 4/2004 | O'Leary |
| 6,729,330 B2 | 5/2004 | Scarrott et al. |
| 6,752,153 B1 | 6/2004 | Eckert |
| 6,761,161 B2 | 7/2004 | Scarrott et al. |
| 6,766,799 B2 | 7/2004 | Edwards et al. |
| 6,769,601 B2 | 8/2004 | Haikarainen et al. |
| 6,907,876 B1 | 6/2005 | Clark et al. |
| 7,004,164 B2 | 2/2006 | Scarrott |
| 7,137,391 B2 | 11/2006 | Bruna |
| 7,143,764 B1 | 12/2006 | Dagsland et al. |
| 7,156,258 B2 | 1/2007 | Eckert |
| 2002/0000225 A1 | 1/2002 | Schuler et al. |
| 2002/0153005 A1 | 10/2002 | Scarrott et al. |
| 2003/0183225 A1 | 10/2003 | Knudsen |
| 2003/0200964 A1 | 10/2003 | Blakley et al. |
| 2003/0205227 A1 | 11/2003 | Hodson |
| 2003/0209239 A1 | 11/2003 | Rand et al. |
| 2004/0065326 A1 | 4/2004 | MacMichael et al. |
| 2004/0069301 A1 | 4/2004 | Bacon |
| 2004/0094147 A1 | 5/2004 | Schyra et al. |
| 2004/0144798 A1 | 7/2004 | Ouyang et al. |
| 2004/0149772 A1 | 8/2004 | Ouyang |
| 2004/0149773 A1 | 8/2004 | Ouyang et al. |
| 2004/0211420 A1 | 10/2004 | Minshull et al. |
| 2004/0221840 A1 | 11/2004 | Stockman-Lamb |
| 2004/0255935 A1 | 12/2004 | Bruna |
| 2004/0255936 A1 | 12/2004 | Urbanus |
| 2005/0011515 A1 | 1/2005 | Lee et al. |
| 2005/0056276 A1 | 3/2005 | Schuler et al. |
| 2005/0268905 A1 | 12/2005 | Rasmussen et al. |
| 2005/0284471 A1 | 12/2005 | Bruna |
| 2006/0254581 A1 | 11/2006 | Genova et al. |
| 2007/0084462 A1 | 4/2007 | Allen |

FOREIGN PATENT DOCUMENTS

| | | |
|---|---|---|
| CA | 535518 | 1/1957 |
| CA | 2 152 088 A | 7/1994 |
| CA | 2 181 789 C | 6/1996 |
| CA | 2 190 204 C | 5/1997 |
| CA | 2 293 484 A | 12/1998 |
| CA | 2 486 892 A1 | 12/1998 |
| CA | 2 315 777 A1 | 7/1999 |
| CA | 2 331 179 A1 | 11/1999 |
| CA | 2 383 425 A1 | 3/2001 |
| CA | 2 388 958 A1 | 3/2001 |
| CA | 2 414 118 A1 | 1/2002 |
| CA | 2 420 171 A1 | 3/2002 |
| CA | 2 480 035 A1 | 10/2003 |
| DE | 6 603 758 | 7/1969 |
| DE | 27 02 539 A1 | 1/1977 |
| DE | 33 36 486 A1 | 4/1984 |
| DE | G 85 90 143.1 | 10/1985 |
| DE | G 86 02 238.5 | 5/1986 |
| EP | 0 028 929 A2 | 5/1981 |
| EP | 0 098 939 A2 | 1/1984 |
| EP | 0 114 617 A2 | 8/1984 |
| EP | 0 063 599 | 6/1986 |
| EP | 0 230 323 B1 | 7/1987 |
| EP | 0 236 871 A2 | 9/1987 |
| EP | 0 269 496 A2 | 6/1988 |
| EP | 0 280 104 B1 | 8/1988 |

| | | |
|---|---|---|
| EP | 0 488 609 A1 | 6/1992 |
| EP | 0 559 757 B1 | 9/1993 |
| EP | 0 752 895 B1 | 7/1998 |
| EP | 0 949 584 A2 | 10/1999 |
| EP | 1 369 139 A1 | 12/2003 |
| EP | 1 220 802 B1 | 2/2004 |
| FR | 2 743 055 | 7/1997 |
| GB | 998 148 | 7/1965 |
| GB | 1 058 636 | 2/1967 |
| GB | 1 290 484 | 9/1972 |
| GB | 1 317 315 | 5/1973 |
| GB | 2 036 695 A | 7/1980 |
| GB | 2 063 075 A | 6/1981 |
| GB | 2 092 991 A | 8/1982 |
| GB | 2 104 393 A | 3/1983 |
| GB | 2 191 032 A | 12/1987 |
| GB | 2 195 544 A | 4/1988 |
| GB | 2 348 928 A | 10/2000 |
| GB | 2 372 543 A | 8/2002 |
| GB | 2 414 187 A | 11/2005 |
| JP | 61-55759 | 4/1986 |
| JP | 04-50059 | 4/1992 |
| JP | 6-26891 | 4/1994 |
| WO | WO 86/02275 | 4/1986 |
| WO | WO 87/04354 | 8/1987 |
| WO | WO 90/10470 | 9/1990 |
| WO | WO 91/06334 | 5/1991 |
| WO | WO 92/07600 | 5/1992 |
| WO | WO 92/09324 | 6/1992 |
| WO | WO 92/15353 | 9/1992 |
| WO | WO 92/17231 | 10/1992 |
| WO | WO 93/24167 | 12/1993 |
| WO | WO 94/11272 | 5/1994 |
| WO | WO 94/14492 | 7/1994 |
| WO | WO 95/26769 | 10/1995 |
| WO | WO 95/34874 | 12/1995 |
| WO | WO 96/16686 | 6/1996 |
| WO | WO 96/16687 | 6/1996 |
| WO | WO 96/39337 | 12/1996 |
| WO | WO 98/01822 | 1/1998 |
| WO | WO 98/56444 | 12/1998 |
| WO | WO 98/56445 | 12/1998 |
| WO | WO 99/36115 | 7/1999 |
| WO | WO 99/57019 | 11/1999 |
| WO | WO 00/09187 | 2/2000 |
| WO | WO 00/59806 | 10/2000 |
| WO | WO 01/28887 A1 | 4/2001 |
| WO | WO 01/29765 A1 | 4/2001 |
| WO | WO 01/37909 A1 | 5/2001 |
| WO | WO 03/101514 A1 | 12/2003 |
| WO | WO 03/103759 A1 | 12/2003 |
| WO | WO 2004/026380 A2 | 4/2004 |
| WO | WO 2004/089451 A1 | 10/2004 |
| WO | WO 2006/110080 A1 | 10/2006 |
| WO | WO 2007/034237 A1 | 3/2007 |
| WO | WO 2007/103712 A2 | 9/2007 |

OTHER PUBLICATIONS

Written Opinion in International Application No. PCT/IB2005/002764, dated Feb. 21, 2006, 5 pages.

U.S. Department of Health and Human Services, Food and Drug Administration, Center for Drug Evaluation and Research (CDER)—Clinical, "Guidance for Industry: Integration of Dose-Counting Mechanisms into MDI Drug Products—Draft Guidance," dated Nov. 2001, 6 pages.

"Geneva drive," Wikipedia [online] [retrieved from internet: URL http://en.wikipedia.org/wiki/Geneva_drive] [retrieved on Sep. 24, 2007], 3 pages.

English language translation of Office Action in Japanese Application No. 2008-019458 dispatched Sep. 29, 2009, 2 pages.

DRIVE MECHANISM FOR AN INDICATING DEVICE

This application claims the benefit of U.S. Provisional Application No. 61/126,436, filed May 5, 2008, the entire disclosure of which is hereby incorporated herein by reference.

TECHNICAL FIELD

The present invention relates generally to an indicating device, and in particular, to a drive mechanism for an indicating device.

BACKGROUND

Various dispensing devices have been developed where it is desirable to provide information about the number of discharges of a particular substance that have been dispensed from or remain in a container. For example, various aerosol dispensing devices have been developed that include a dose indicating device to indicate the number of metered doses that have been dispensed from the device, or to indicate the number of doses remaining therein. For example, patients have certain conditions that can be treated with medicaments dispensed in an aerosol and administered to the patient by inhalation. In one format, the aerosol with medicaments are contained in a container, and dispensed in metered, or measured, dosages with an inhalation device, or actuator boot. In such an arrangement, it can be important for the patient to be able to ascertain the number of metered doses remaining in the container, either by an indication of the number remaining therein or by knowledge of the number already dispensed therefrom, such that the patient is not caught unaware with an empty container when in need of the medicament. Thus, it may be important for the inhalation device to provide an accurate indication of either the number of doses remaining in the container, or the number of doses already dispensed therefrom.

In order to provide an accurate indication, some devices are provided with an indexing device that prevents an indicator member from inadvertently moving when the device is not being actuated, for example when the device is dropped or otherwise jarred, or if the indicator member is designed to move only upon a predetermined number of actuations greater than one. At the same time, it may be desirable to provide a relatively uniform actuation force for the dispensing device, regardless of whether the indicator member is being advanced by overriding the indexing device, or is not being advanced, for example when the indicator member is immobilized between the number of predetermined actuations.

SUMMARY

Briefly stated, one preferred embodiment of an indicating device includes a drive member rotatable about a first rotation axis. The drive member has a convex surface extending at least partially circumferentially about the first rotation axis and a recess opening radially inwardly from the convex surface. The drive member also includes an engagement member. A driven member is rotatable about a second rotation axis. The driven member has a plurality of concave surfaces successively engaged by the convex surface of the drive member. The driven member is non-rotatably immobilized about the second rotation axis by the successive engagement of the convex surface with the plurality of concave surfaces as the drive member rotates about the first rotation axis. The driven member further includes a plurality of protrusions formed between adjacent ones of the plurality of concave surfaces. Each of the plurality of protrusions are successively received in the recess as the engagement member engages the driven member and rotates the driven member about the second rotation axis. In one embodiment, the driven member further includes dispensing indicia.

In yet another aspect, a preferred embodiment of a method for indicating the amount of substance that has been dispensed from or remains in a container includes rotating a drive member about a first rotation axis, wherein the drive member has a convex surface extending at least partially circumferentially about the first rotation axis and a recess opening radially inwardly from the convex surface. The method further includes engaging a driven member with the drive member and thereby rotating the driven member an incremental amount about a second rotation axis, wherein the driven member has a plurality of concave surfaces and a plurality of protrusions formed between adjacent ones of the plurality of concave surfaces. The method further includes disposing one of the plurality of protrusions in the recess as the driven member is engaged and rotated the incremental amount by the drive member, and slidably engaging one of the concave surfaces of the driven member with the convex surface of the drive member and thereby preventing the driven member from rotating about the second rotation axis. The method further includes displaying dispensing indicia on the driven member.

In another aspect, one embodiment of an indicating device includes an indicator member having dispensing indicia. The indicator member is rotatable about a first rotation axis and includes a plurality of stop surfaces. A stop member is rotatable about a second rotation axis. The stop member is selectively engaged with successive ones of the plurality of stop surfaces, wherein the indicator member is non-rotatable about the first rotation axis when the stop member is selectively engaged with one of the plurality of stop surfaces.

In yet another aspect, one embodiment of a method for indicating the amount of substance that have been dispensed from or remain in a container includes successively rotating an indicator member an incremental amount about a first rotation axis, wherein the indicator member includes dispensing indicia and a plurality of stop surfaces. The method further includes successively rotating a stop member an incremental amount about a second rotation axis, and selectively engaging successive ones of the plurality of stop surfaces with the stop member between the successive rotations of the indicator member and thereby preventing the indicator member from rotating about the first rotation axis.

The presently preferred embodiments provide significant advantages over other dispensing devices and indicating devices used therewith. In particular, the engagement between the drive member and the driven member, or between the stop member and the indicator member, prevents the driven member and indicator member from being inadvertently moved respectively. At the same time, the successive reception of each of the plurality of protrusions on the driven member in the recess of the drive member does not provide any resistive force that is required to be overcome when moving the driven member.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

DETAILED DESCRIPTION OF THE PRESENTLY PREFERRED EMBODIMENTS

Figure 1:
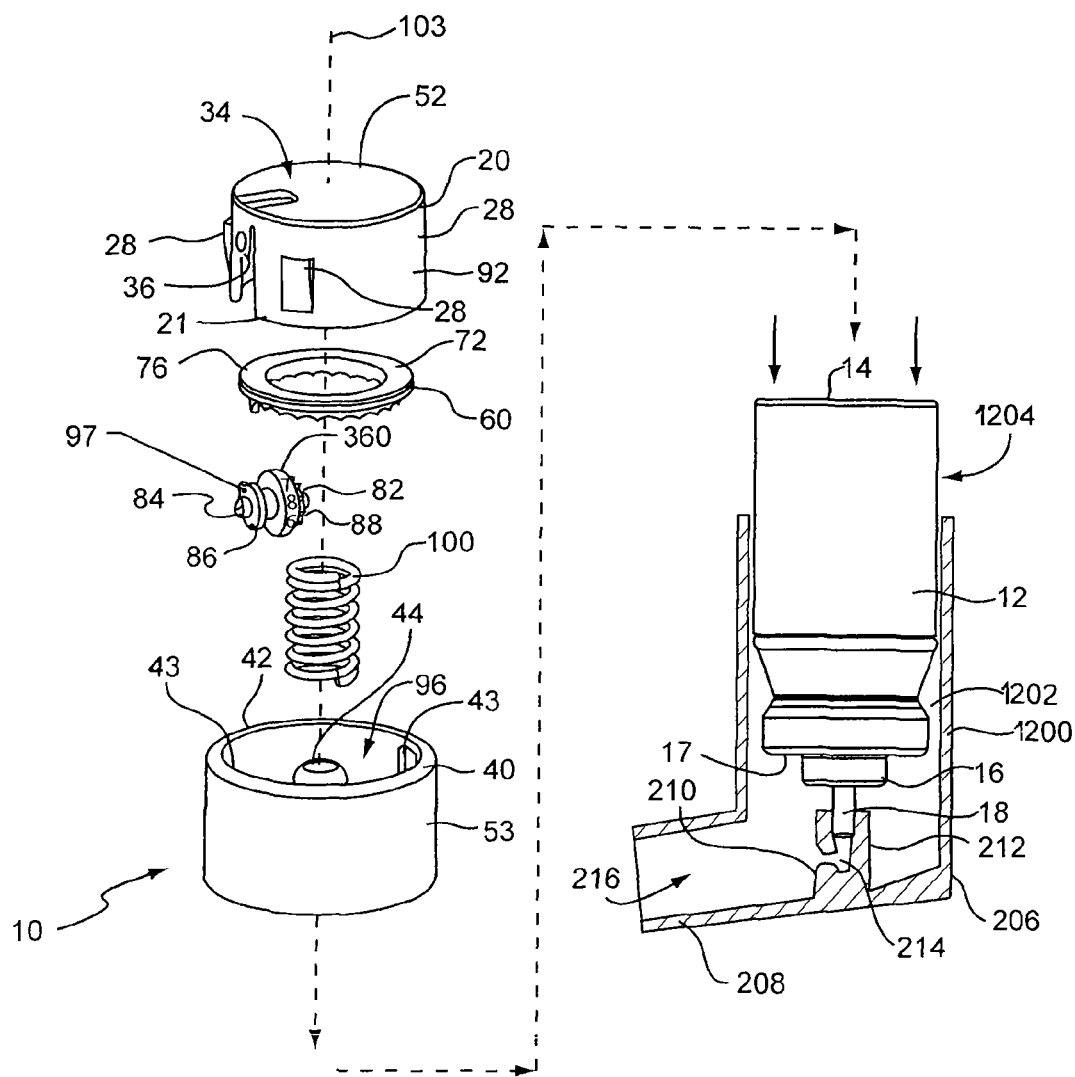
FIG. 1 is an exploded view of an indicating device and a container supported in a dispenser housing shown in cross-section.

Referring to the drawings, and in particular FIG. 1, an aerosol dispenser shown as including a housing 1200, or actuator boot, and a container 12 disposed therein. The housing has a longitudinally extending cavity 1202 shaped to receive the container. The top portion of the housing is generally open such that the container can be inserted in the housing through opening 1204 and be installed therein with a bottom end 14 of the container protruding from the housing so as to be exposed to the user for actuation.

The terms "longitudinal" and "axial" as used herein are intended to indicate the direction of the reciprocal movement of the container relative to the housing, and of an indicating device cap member relative to a base member. The terms "top," "bottom," "upwardly" and "downwardly" are intended to indicate directions when viewing the inhalation devices as shown in the Figures, but with the understanding that the container is inverted such that the top surface thereof is located adjacent the bottom of the housing and vice versa. Moreover, it should be understood that a user can use the container and dispenser in any number of positions, including but not limited to the preferred upright position shown in FIG. 1.

As shown in FIG. 1, a cylindrical support block 212 having a well 214 is formed in a bottom portion 206 of the housing. An orifice 210 penetrates the support block to communicate with a bottom portion of the well. In one embodiment, a mouthpiece 208, intended for insertion into the mouth of a patient, forms an exhaust port 216 that communicates with the orifice and well. The mouthpiece 208 extends laterally from the housing so as to facilitate insertion of the mouthpiece into the mouth of the patient.

The container 12 is cylindrical and has a hub 16 disposed on a top surface 17 thereof. A valve stem 18 extends longitudinally from the hub. The valve stem extends coaxially from the container and is biased outwardly therefrom by a spring (not shown) mounted within the valve stem of the container. The container 12 is mounted in the housing by press fitting the valve stem 18 in the well 214 of the support block.

In a preferred embodiment, the container 12 is filled with a pressurized aerosol and medicament which is dispensed therefrom in specific metered doses by an actuation thereof effected by depressing or moving the valve stem 18 from an extended closed position to a depressed open position. A single metered dose is dispensed from the container by each reciprocal, longitudinal movement of the valve stem, or actuation of the container.

In operation, the opening of the valve stem is effected by moving the container 12 reciprocally within the housing 1200 along a longitudinal axis, defined by the valve stem and the reciprocal movement of the container, by depressing the bottom end 14 of the container relative to the housing so as to move the valve stem 18 to the open position as it is supported within the well by the support block. As the valve stem is moved to the open position, the container dispenses a metered dose of aerosol and medicament through the well 214 and orifice 210. The aerosol and medicament are then transmitted to the patient through the exhaust port 216 by the mouthpiece by way of either a self-generated or assisted airflow.

In other delivery systems, the housing and holder for the container are attached to a component having a chamber with an output end. Examples of these kinds of delivery systems are shown for example in U.S. Pat. No. 5,012,803, issued May 7, 1991, and U.S. Pat. No. 4,460,412, issued Sep. 11, 1984, both of which are hereby incorporated herein by reference. (No license, expressed or implied, is intended to be granted to either of these patents by reason of the incorporation by reference herein). In these kinds of delivery systems, the component having the chamber can be adapted to receive the mouthpiece of the housing, or it can be integrally connected with a holder supporting the container. In either embodiment, the metered dose of medicament in aerosol is first dispensed from the container into the chamber, and thereafter inhaled by the patient.

In a preferred embodiment, the container 12 is intended to dispense a predetermined number of metered doses of medicament upon a corresponding number of predetermined actuations of the container. For example, conventional inhaler containers typically hold on the order of 100 to 200 metered doses. It should be understood, however, that the range of available doses could potentially vary from as few as one dose to as many as 500, or even more, depending, for example, on the capacity of the container, and/or the size of the metering dose valve. In operation, it can be important for the patient to be aware of the number of metered doses remaining in the container such that the patient is not caught unaware with an empty container when in need of the medicament. It should be understood that other dispensing devices, other than aerosol devices, are configured to sequentially dispense substances, including without limitation other medical dispensing devices such as powder inhalers and other dispensers.

Now generally referring to the Figures, a dispenser indicating device is shown. The indicating device 10 indicates, for example, the number of metered doses that have been dispensed from or remain in the container. As shown in the embodiment of FIG. 1, respectively, the indicating device 10 includes an indicating device housing comprised of a cap member 20 disposed in a base member 40. The base member 40 is configured such that it can be mounted to the bottom end 14 of the container 12. In one embodiment, the base member 40 includes a convex, or curved bottom portion, or floor, which is shaped to be received in and to mate with the bottom end 14 of the container, which has a concave or inwardly curved contour. The base member 40 is preferably bonded to the bottom of the container with adhesive, double sided tape, or similar bonding agent. In one embodiment, an adhesive wrap, such as a label, is wrapped around the indicating device and container, which in one embodiment have substantially the same outer diameter. In other embodiments (not shown), the base member can be configured with a downwardly depending circumferential skirt, which is shaped to receive the bottom end of the container. In such an embodiment, the base member is mounted on the container either by bonding one or more of the bottom portion or skirt to the container, and/or by press fitting the container in the base member so as to provide an interference fit between the container and the depending skirt.

Although the disclosed container and indicating device, and in particular, the cap member and base member, are shown as preferably having a circular cross section, those skilled in the art should understand that the container and indicating device, including any adapter, can be configured in other shapes, including for example, but not limited to, a rectangular or triangular cross-section. In addition, it should be understood that the base member can be moveably received in the cap member. Various indicating devices are shown in U.S. Pat. No. 7,004,164, issued Feb. 26, 2006, and U.S. Pat. No. 6,729,330, issued May 4, 2004, the entire disclosures of which are hereby incorporated herein by reference.

As best shown in FIG. 1, the cap member 20 has a top portion 52 with a viewing window 34 formed therein. Preferably, the cap member 20 is circular in cross-section and the viewing window is formed in the top portion adjacent the outer periphery of the cap member so as to overlie indicia applied to first and second indicator members 60, 360 supported beneath the cap member. The viewing window 34 can be configured in a number of various shapes. For example, the viewing window can be tapered, arcuate shaped (bounded by coaxial inner and outer curved borders and radial side borders), or any other suitable shape. The top of the cap member preferably has a plurality of raised portions forming a grippable pattern for the user's thumb, or finger. In this way, the user can firmly press down on the cap member without slippage. One of skill in the art should recognize that other patterns or grippable surfaces, such as a knurled pattern, can be applied to the cap member to facilitate the use of the indicating device.

Referring to FIG. 1 the cap member 20 includes a circumferential skirt 92 depending downwardly from the top portion 52. The skirt preferably has a smaller diameter than an upwardly depending skirt of the base member 53, such that the cap member skirt nests within the upwardly extending skirt of the base member. Alternatively, the cap member can be configured with a skirt having a larger diameter than the skirt of the base member such that the base member skirt nests in the cap member skirt. The cap member 20 is moveably mounted to the base member 40 by way of a snap fit.

In particular, the cap member includes a plurality of engagement members 28 extending from an outer circumferential surface of the skirt. The cap member 20 is inserted axially within a recess or cavity 96 of the base member such that the engagement members 28, which have a tapered surface, slide past a rim 42 of the base member skirt until the engagement members are disposed in a plurality of pockets 43 formed along the inner circumferential surface of the base member skirt to form a snap-lock fit. In particular, the upper surface of the engagement member 28 engages an engagement surface defining the top of the pocket 43. In this way, the cap member 20 is moveable with respect to the base member 40 along an axial, or longitudinal, path. Alternatively, the rim of the base member can be curved slightly inward such that the engagement members engage the inwardly curved rim portion so as to prevent the cap member from being separated from the base member.

The axial movement of the cap member 20 relative to the base member 40 is bounded or constrained by the engagement of the engagement members with the top of the base member pockets (or the base member rim) at a fully extended position and by engagement of a bottom rim 21 of the cap member skirt with a surface of the bottom portion of the base member at the bottom of the stroke. One of skill in the art should understand that the engagement members can alternatively be formed on the base member skirt so as to engage pockets or openings, or a rim (or like protrusion), formed on the cap member skirt.

As shown in FIG. 1, a spring 100 is disposed between the cap member and the base member. The spring is preferably disposed around an upwardly extending hub portion 44 of the base member, which mates with a hub portion of the cap member. The spring 100 functions as a return mechanism and biases the cap member 60 upwardly in the base member such that the engagement members 28 of the cap member engage the upper portion of the pockets of the base member. Although a compression spring is shown in the Figures, it should be understood that a belleville washer, cantilever, torsion, leaf and/or tension springs would also work to bias the cap member upwardly into engagement with the base member. The springs can be made of metal or plastic.

Referring to FIGS. 1-3D, a first indicator member 60 is rotatably mounted in the cap member 20 about an axis 103 substantially parallel to the axial movement of the cap member relative to the base member, and preferably coaxially therewith. In this way, it should be understood that the term "parallel" refers to two axes extending in the same direction, whether spaced apart or coaxial. The indicator member is also referred to herein as a driven member. The indicator member is generally open in the middle and includes an annular ring portion 76 having an upper surface that rotatably slides along a bottom surface of the top portion of the cap member. Alternatively, the indicator member can be mounted on the outside of the cap member with a viewing window formed in the indicator member for viewing indicia applied to the top of the cap member.

The annular ring portion 76 of the indicator member is rotatably secured to the cap member with a plurality of protrusions (not shown), or tab members, which extend from an inner circumferential surface of the cap member skirt. Alternatively, the indicator member can include an engagement member, or rim, that engages a groove or similar opening in the cap member. In this way, the indicator member is secured to the cap member so as to prevent axial movement therebetween but wherein the indicator member 60 is permitted to rotate relative to the cap member 20. The indicator member is installed by snap-fitting the indicator member within the cap member. One of skill in the art should understand that the indicator member could alternatively be rotatably mounted on the cap member hub portion, or on a similar axle secured to the cap member.

Figure 2:
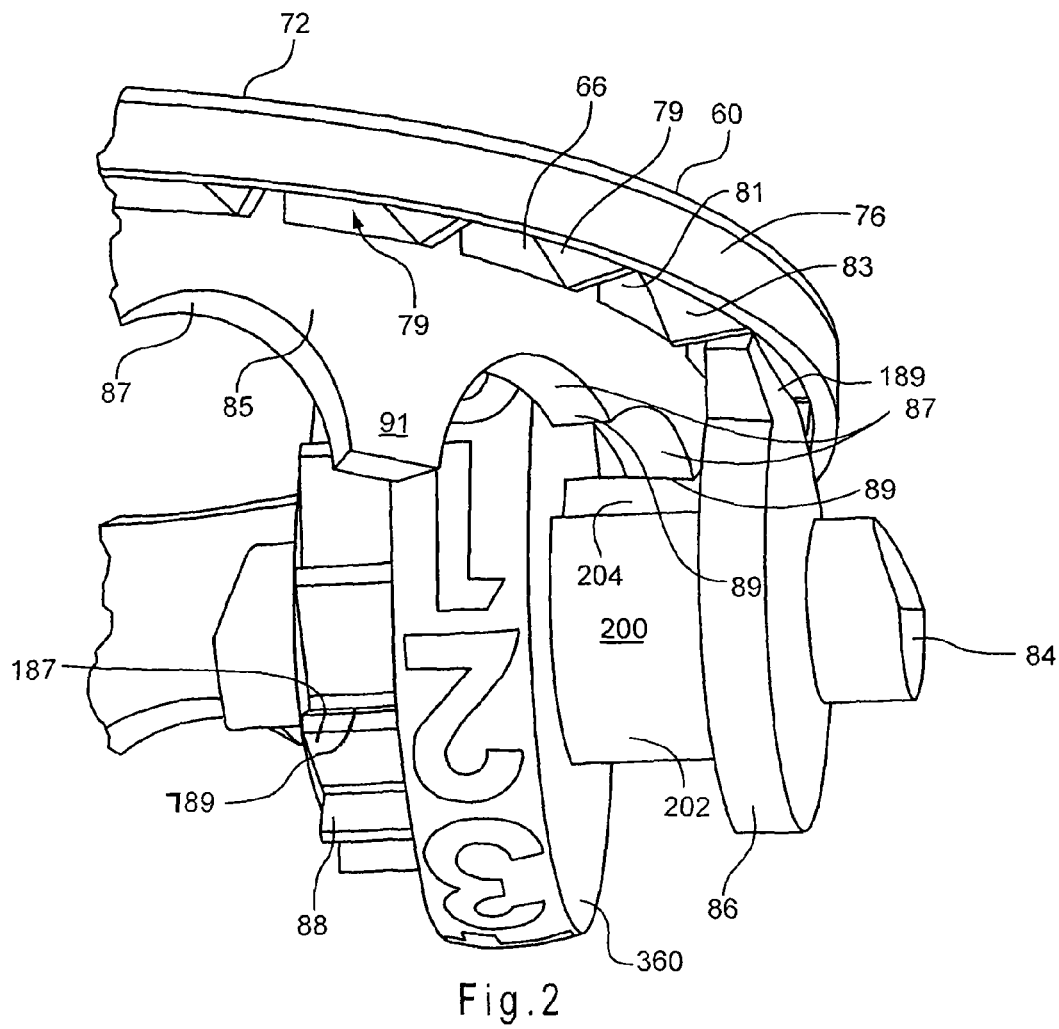
FIG. 2 is an enlarged partial perspective view of an indicator member and drive mechanism.
Figure 3A:
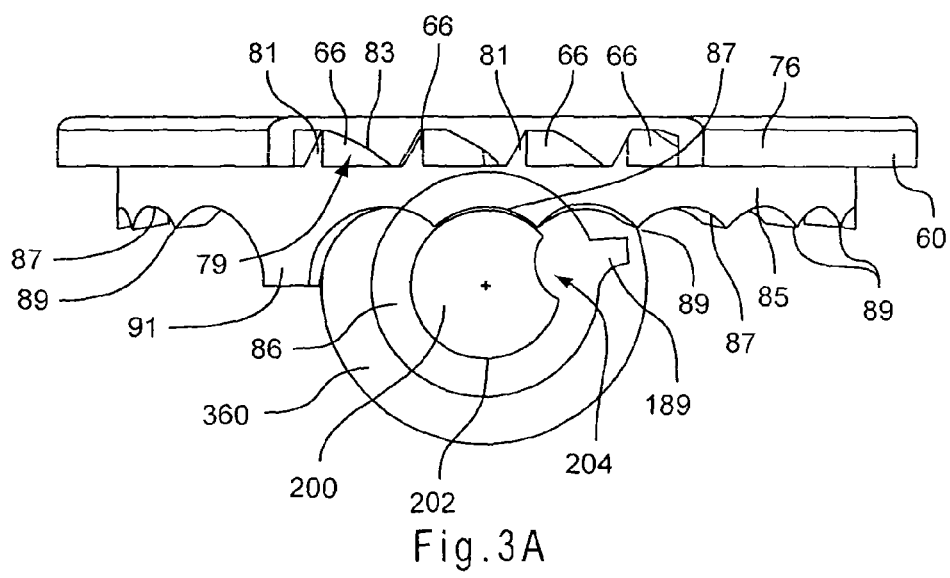
FIGS. 3A-3D are side views of one embodiment of an indicator member and drive mechanism shown during successive actuations of the drive mechanism.
Figure 3B:
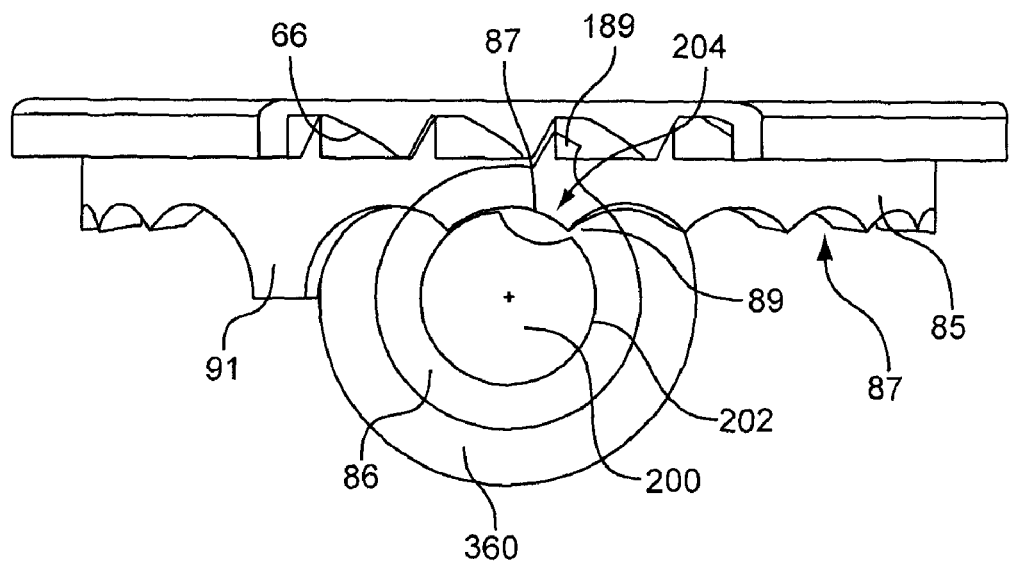
Figure 3C:
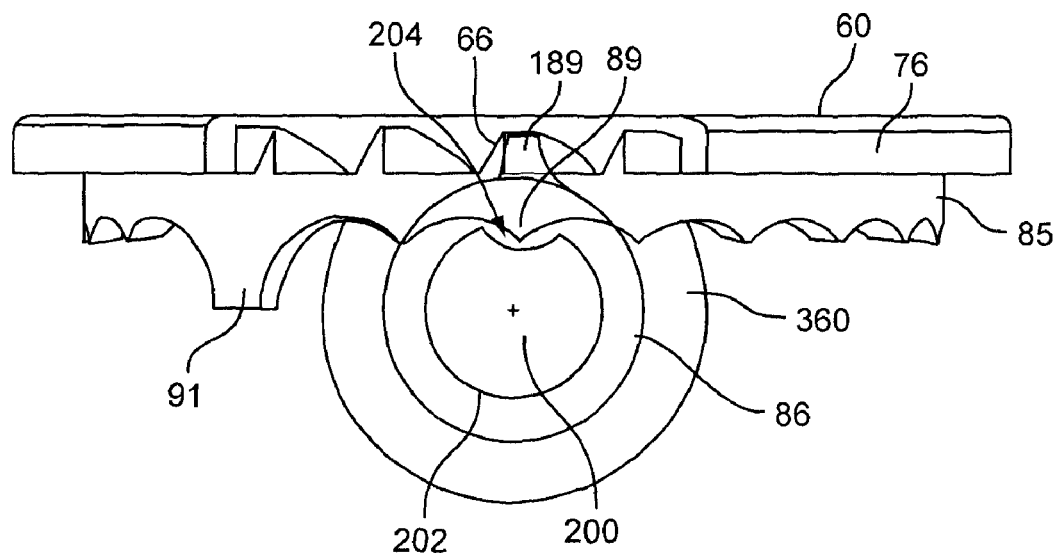
Figure 3D:
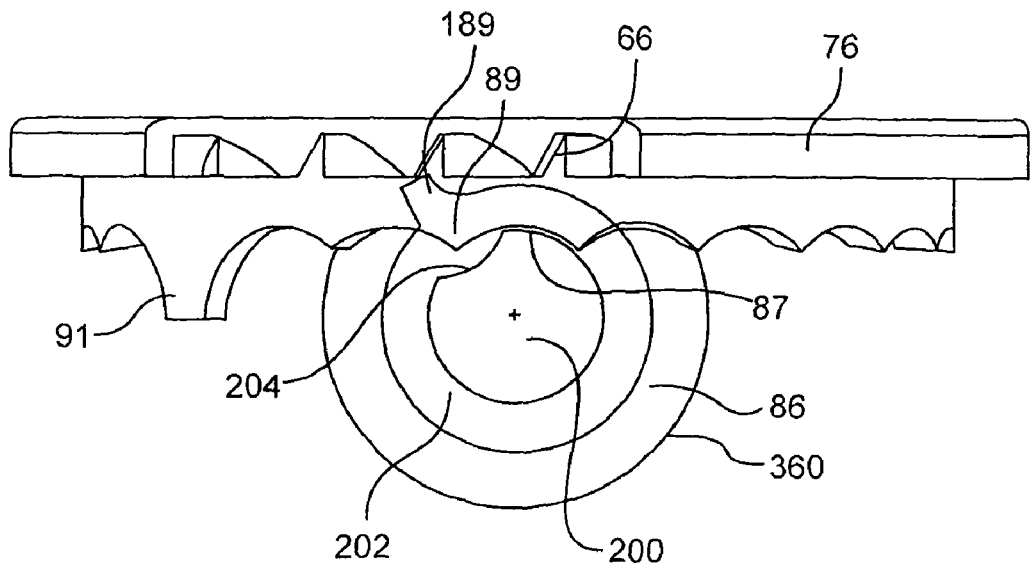

As shown FIGS. 2-3D, the indicator member 60 has a plurality of downwardly facing teeth 66 formed around the outer periphery on a bottom side of the annular ring member. The teeth are formed by recesses 79 formed in the bottom of the annular ring member 76, with each recess having a leading engagement face 81 and a curved trailing surface 83. The teeth 66 are formed in a circumferential ring around the periphery of the ring member 76.

The indicator member 60 further includes a circumferential skirt 85 extending downwardly from the annular ring 76. In one embodiment, the skirt is positioned radially inwardly from the teeth. A bottom rim portion of the rim is configured with a plurality of recesses, forming concave stop surfaces 87, and protrusions 89 formed between adjacent ones of said plurality of concave surfaces. It should be understood that the term "concave" as used herein means rounded inward, and preferably is formed as a smoothly curved surface, although it can also be formed by various linear surfaces, for example various linear segments. The protrusions 89 are formed, in one embodiment, by the intersection of the concave surfaces 87. The concave surfaces 87 open longitudinally downwardly, and the protrusions 89 extend longitudinally downwardly. In one embodiment, the concave surfaces 87 are defined as a portion of a circle, with the centers of adjacent circles defining the concave surfaces spaced apart a distance less than the diameter of the circles, such that the surfaces 87 intersect to form the protrusions 89. At one location, the centers of two adjacent circles are spaced apart a greater distance than the length of the diameter of each circle such that the concave surfaces do not intersect, but rather form an enlarged protrusion 91 having a greater length than each of the plurality of other protrusions. The distance between the centers of the circles defining the concave surfaces 87 is preferably approximately the same as the distance between adjacent teeth 66, such that there is a one-to-one correlation between the concave stop surfaces 87 and the teeth 66.

As shown in FIG. 1, dosage indicia 72 in the form of numbers or color codings are provided on the top surface of the indicator member and are visible to the user through the viewing window 34 provided in the top of the cap member. In one embodiment, the indicia are configured as numbers arranged sequentially from 0 to 21 around the upper surface of the annular ring 76. It should be understood that other indicia indicating the number of doses remaining in or dispensed from the container would include, but not be limited to, various alpha-numerical characters, words, terms or phrases (such as "full" and "empty"), scales, grids, arrows, raised portions, indentations, color coding and segmentation, shading and like markings, or any combination thereof. For example, a segmented color grid displayed in the viewing window could turn from green, indicating a full container, to yellow, indicating an intermediate capacity, and finally to red, indicating an empty container. It should also be understood that the indicia can be formed integrally with the counter member, or applied thereto by means of paint, dye, etching, pad printing, hot stamping or adhesive labels. When using numerical indicia, the numbers can be arranged to go from 0 (or some beginning number) to the predetermined number of available doses such that a display of that number to the user indicates that the container should be replaced, or, conversely, to go from the starting predetermined number to 0 (or some ending number), which again indicates to the user that the container should be replaced.

In a preferred embodiment, the indicator member is made of acrylonitrile butadiene styrene ("ABS"), which is receptive to certain alternative processes of printing or applying the indicia, including pad printing and hot stamping. The cap member and base member are preferably made of a hard plastic material such as Acetel. In various preferred alternative embodiments, one or both of the base member and cap member can be made of polycarbonate.

Referring to FIGS. 1-3D, a drive mechanism is shown as including a drive assembly 97. The drive assembly includes a ratchet wheel 82 coaxially mounted to a drive member 86 on an axle 84. The ratchet wheel, drive member and axle can be made separately, with the ratchet wheel and drive member then mounted on the axle, or all three parts can be integrally molded as a one-piece component. The drive assembly is preferably made of hard plastic material such as Acetel. The drive assembly further includes a second dosage indicator member 360 coaxially mounted with and between the drive member 86 and ratchet wheel 82. The indicator member 360 is configured as a wheel and preferably includes dosage indicia positioned around the peripheral surface thereof. Preferably, the indicia are comprised of consecutive numerals running from 0 to 9, and provide dispensing indicia to the user in combination with indicator member 60.

The ratchet wheel 82 includes a plurality of teeth 88 (preferably ten) formed around its periphery. Each of the teeth includes an engagement surface 789 and a tapered surface 187. The drive member 86, whether integrally formed with the ratchet wheel or separately connected thereto, includes a single tooth 189 extending radially from the axle 84.

In the embodiments shown in FIG. 1, the drive assembly 97 is mounted to the cap member by engaging opposite ends of the axle 84 with downwardly extending hub portions 36 such that the axle, ratchet wheel and drive member rotate about an axis substantially perpendicular to the axial movement of the cap member relative to the base member and to the axis of rotation of the indicator member. Alternatively, the drive assembly can be mounted to the base member, along with the indicator member, in a similar manner.

Figure 4:
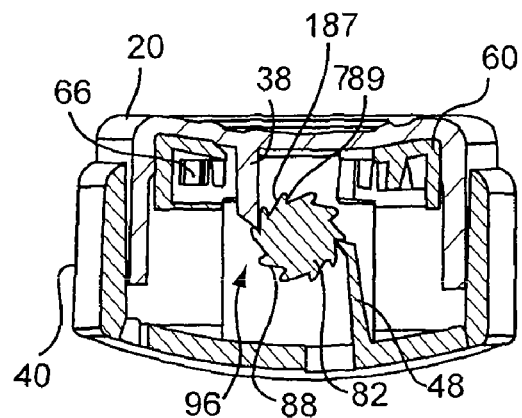
FIG. 4 is a cross-sectional view of the indicating device.

As shown in FIG. 4, the drive mechanism further includes a pawl member 48, shown as a flexible rod or finger, which extends upwardly from the bottom portion of the base member and selectively engages one of the teeth of the ratchet wheel. Alternatively, the pawl member can be moveably secured to the cap member and extend through the base member to engage the top of the container, such that the axial movement of the cap member toward the container causes the pawl to move toward the ratchet wheel and engage one of the teeth thereon as described below. A non-return member, also shown as a flexible rod or finger, extends downwardly from the top portion of the cap member and selectively engages another of the teeth 88 of the ratchet wheel. It should be understood that the pawl member could alternatively extend from the cap member (and the non-return member from the base member) when the drive assembly is mounted to the base member, as described above. Of course, when formed integrally with one or the other of the cap member and base member, the pawl member and non-return member are preferably made of the same materials as the respective cap member and base member.

In operation, the user depresses the cap 20 member from a fully extended position toward the base member such that the cap member bottoms out in the base member at the bottom of the stroke and such that the base member imparts an axial load on the container until a metered dosage is dispensed therefrom. In a preferred embodiment, the biasing force of the spring 100, or alternative return mechanism such as the resilient arm members which act as springs, is less than the biasing force of the spring located in the metering valve of the container, such that the cap member first bottoms out in the base member with the container then being moved downwardly in the housing until a metered dose is dispensed.

As the cap member 20 is depressed toward the base member 40, the pawl 48 selectively engages the engagement surface 789 of one of the ratchet wheel teeth and rotates the ratchet wheel. The tapered surface 187 of one of the teeth formed on the ratchet wheel simultaneously biases the non-return member 38 outwardly until it selectively engages the next tooth near the bottom of the stroke. The non-return member 38 provides an audible click as it engages the next tooth. The user then releases the cap member whereinafter the spring 100, or similar return mechanism, biases the cap member 20 away from the base member 40 until the engagement member engages the base portion at the top of the stroke. When the cap member is released by the user, the container is biased upwardly within the housing along the longitudinal axis such that the valve stem is moved to the closed position within the container. Simultaneously, as the cap member is released and allowed to move away from the base member, the pawl 48 is biased outwardly by the tapered surface 87 of one of the teeth on the ratchet wheel as the non-return member 38 prevents a backwards rotation thereof so as to maintain a unidirectional rotation of the ratchet wheel. At the top of the stroke, the pawl 48 is again placed in position for selective engagement with one of the teeth of the ratchet wheel. Again, the pawl provides an audible click as it engages the next tooth. In summary, on the down stroke the non-return member makes a clicking sound as it slides over one or more ratchet teeth, while on the up stroke, the pawl member also makes a clicking sound as it slides over one or more ratchet teeth. In this way, the ratchet wheel 82, and connected drive member 86, are advanced an incremental amount for every actuation of the container and the attendant release of medicament. The incremental amount is defined by and dependent on the number of teeth formed about the periphery of the ratchet wheel. When formed with ten teeth, as shown in the preferred embodiment, the ratchet wheel will make one full revolution for every ten actuations of the indicator device and container, or a tenth of a revolution for each actuation. It should be understood that the ratchet wheel can be provided with various numbers of teeth formed about its periphery such that the more or less axial movements or actuations of the container are required to make one full rotation of the ratchet wheel.

Alternatively, the operation of the ratchet wheel can be reversed. In this embodiment, the pawl is biased outwardly by the tapered surface of one of the ratchet wheel teeth on the downstroke. At the bottom of the stroke, the pawl is biased into engagement with one of the teeth. When the cap member is released by the patient, the spring, or equivalent return mechanism, biases the cap member upwardly within the base member along the longitudinal axis such that the pawl member engages one of the teeth and thereby rotates the ratchet wheel an incremental amount. In this embodiment, the non-return member maintains the rotational position of the ratchet wheel on the downstroke.

As shown in FIGS. 1-3D, the drive member 86 is shown as preferably having a single tooth 189 or segment. Therefore, upon every tenth actuation, the drive member 86 is rotated such that the tooth selectively engages one of the teeth 66 formed on the indicator member so as to rotate the indicator member 60 an incremental amount. The incremental amount of rotation is defined by the distance between adjacent teeth 66, otherwise defined as the circular pitch of the teeth. In this way, the drive member is selectively engaged with at least one of the teeth of the indicator member after and upon a predetermined number of axial movements of the cap member relative to the base member so as to rotate the indicator member the incremental amount. The predetermined number axial movements required to cause the indicator member to rotate is defined by and dependent upon the reduction ratio of the ratchet wheel and drive member, which, in turn, is defined by dividing the number of teeth formed on the ratchet wheel by the number of teeth formed on the drive member. For example, as shown in the preferred embodiment, a ratchet wheel having ten teeth and a drive member having one tooth will result in an incremental movement of the indicator member, otherwise defined as the advancement of one tooth of the indicator member, upon every ten axial movements. Similarly, if the drive member had four teeth, and the ratchet wheel twenty, the predetermined number would equate to five axial movements, and so on. A one-to-one gear ratio would result in a predetermined number of one axial movement, wherein the indicator member would be moved upon every axial movement.

As shown in the embodiment of FIGS. 1 and 2, the ratchet wheel includes ten teeth. As the container is actuated ten times, the drive tooth 189 rotates around until it engages one of the teeth 66 on the indicator member 60. At this point, the indicator has completed a single cycle equal to the number of predetermined number of axial movements, which results or culminates in the incremental movement of the indicator member 60. The cycle is then repeated (by again making the predetermined number of axial movements) so as to again culminate in the incremental movement of the indicator member. Preferably, as shown in FIG. 1, numerical indicia (tens counter) 0-21 are applied so as to correlate to the preferred embodiment requiring ten axial movements for one incremental advancement of the indicator wheel, with numerical indicia 0-10 applied to the outer peripheral surface of the second indicator member 360.

The ratchet wheel 82 and drive member 86 with their reduction ratio provide a simple but reliable mechanism for advancing the indicator member. In particular, the indicator member can be made with fewer teeth than if it were required to advance upon every actuation of the indicator member and container. For ease of manufacturing, it is desirable to provide as coarse a pitch on each of the indicator member and ratchet wheel as possible, although the gears are still defined as fine-toothed gears. However, it is also intended that the indicator member make only a single revolution (single-cycle) corresponding to a complete evacuation of medicament from the container. Thus, when a large number of doses (on the order of 200 or more) are contained within the container, it is important for the ratchet wheel and drive member to provide a relatively high reduction ratio, such that 200 linear reciprocal movements of the cap member and container correspond to one or less revolutions of the indicator member 60. As such, the indicator member can be made with coarser teeth at less cost. In addition, larger coarser teeth interacting with a relatively large drive member tooth 189 helps to improve the accuracy of the device as those parts mesh. In addition, the mechanism, and its attendant reduction ratio, permits the indicator member to make only a single revolution during the life of the container, i.e., until it is emptied, even when the container contains a relatively large number of metered doses (on the order of 200 or more doses). This single revolution corresponds to a usage cycle, which is defined as the movement of the dosage indicator from an initial reading, which indicates that the container is full, to a final reading, which indicates that the container should be replaced. Of course, the indicator member, if initially set to a smaller number of dosages, may make less than a complete revolution in completing a usage cycle.

As shown in FIG. 1, the viewing window 34 is large enough such that the first and second dosage indicator members 60, 360 with their indicia are visible therein. In the operation of these embodiments, the indicator member 360 rotates with each actuation of the cap member 20 relative to the base member 40 as the ratchet wheel 82 is driven by the pawl member 48. The indicator member 360 rotates about an axis substantially perpendicular to the axial movement of the cap member relative to the base member and to the rotational axis of the indicator member. In the preferred embodiment, with the indicator member 360 having "ones" indicia and the ratchet wheel 82 having ten teeth, the indicator member 360 is advanced upon each actuation and provides indicia visible to the user to notify them of such advancement. As the indicator member 360 completes a cycle, or rotation, the indicator member 60 is advanced one increment by the drive member 86 and the indicator member 360 begins another cycle. In this way, the user is advised as to each actuation of the indicating device and the attendant dispensment of a dosage from the attached container.

As shown in FIGS. 2-3D, the drive member includes a stop member 200 spaced laterally between the drive member 86 and the indicator member 360. The stop member 200 is formed as enlarged circular portion having a convex surface 202, with a recess 204 extending radially inwardly from the convex surface. The term "convex" as used herein means protruding or rounded outwardly, for example like the exterior of a circle or other curved surface, or alternatively is formed by various linear segments. The recess can be formed as a concave-shaped recess, or as any other shape or simply an opening in the convex surface or a wall defining the convex surface. For example, the stop member can be formed as a thin circumferential wall having an opening formed therein. The convex surface 202 preferably has a contour that is substantially the same as and mates with the contour of the concave surfaces 87 of the indicator/driven member. For example, the convex and concave surfaces 87, 202 may have substantially the same radius or diameter, or the concave surface 87 may have a slightly larger radius or diameter than the convex surface 202.

In operation, the user moves the cap member 20 toward the base member 40 a first predetermined number of times corresponding to the total number of metered dosages, such that the indicator members 60, 360 are rotated between an initial position, wherein indicia indicate to the user that the container is full, and a final position, wherein the indicia indicate to the user that the container should be replaced. During the first predetermined number of actuations, the drive member 86, and in particular, the tooth 189, is successively engaged with at least one of the teeth 66 of the indicator member upon a second predetermined number of axial movements of the cap member 20 relative to the base member 40, wherein the indicator member 60 is moved an incremental amount. Preferably, the first predetermined number of actuations is greater than and some multiple of the second predetermined number of actuations. However, it should be understood that the first and second predetermined number of actuations can be equal, preferably with the second predetermined number being greater than one.

Referring to FIGS. 3A-3D, the convex surface 202 of the stop member 200 slidably engages one of the concave surfaces 87 of the driven member 60 as the drive member 86 is successively rotated. The engagement between the concave and convex surfaces 87, 202 prevents the indicator driven member 60 from being rotated about the longitudinal axis during each cycle of second predetermined number of actuations (see, e.g., FIG. 3A). As the drive tooth 189 is rotated around to engage the one of the teeth 66 on the indicator member 60, one of the protrusions 89 between adjacent ones of the plurality of concave surfaces 87 is simultaneously disposed in the recess 204 formed in the stop member, such that the stop member 200 is disengaged from the indicator member 60, thereby permitting the drive tooth 189 to engage one of the teeth 66 on the driven indicator member 60 and advance the driven indicator member 60 an incremental amount (see, e.g., FIGS. 3B and 3C). In one embodiment, the drive tooth 189 and recess 204 are angularly aligned along a common radius. As the drive tooth 189 disengages from the driven indicator member 60, the convex surface 202 of the stop member is brought into slidably engagement with a next adjacent one of the curved concave surfaces 87 so as to again immobilize the indicator member 60 and prevent it from rotating (see, e.g., FIG. 3D). Because the stop member 200 is disengaged from the indicator member 66 while the driven indicator member 60 is being advanced an incremental amount by the drive tooth 189, the stop member 200 does not increase the amount of force needed to advance the driven indicator member 60. In addition, the slidably engagement between the convex and concave surfaces 202, 87 is relatively frictionless, such that the engagement therebetween prevents the indicator member 60 from being rotated, but does not increase the force required to rotate the drive member 86 and attached indicator member 360.

At the end of the entire usage cycle, the enlarged protrusion 91 on the driven indicator member 60 is too large to be received in the recess 204 of the stop member 200, such that the protrusion 91 prevents the indicator member 60 from being rotated any further and thereby locks up the indicating device.

Upon the next subsequent actuation of the container 12 after the final predetermined actuation, the cap member 20 is again moved toward the base member 40. However, since the drive member 86 is locked and unable to rotate, the engagement surface 789 of one of the teeth on the ratchet wheel engages the pawl 48 and deforms the pawl, preferably by bending, as the cap member 20 moves toward the base member 40. As such, neither the non-return member 38 nor the pawl 48 moves past any teeth of the ratchet wheel 82 and the audible click is thereby eliminated. In this way, an auxiliary warning system, or indicia, is provided to inform the user that the final predetermined dose of medication has been dispensed, and/or that the container should be replaced. At the same time, however, the container can still be actuated, such that if certain residual doses were available therein they can be dispensed in an emergency situation. In addition, the bent pawl 48 prevents tampering and unintended resetting by the user.

In one embodiment, the pawl 48 has fillets formed along its base each having a preferred radius of about 1.40 mm, or preferably a radius greater than a minimum value required to prevent stress concentrations in the plastic during the bending process that occurs during the next subsequent actuation or movement of the cap member after the final predetermined actuation of the container. The overall height of the pawl is preferably about 5.20 mm. The width of a pawl head is preferably about 1.80 mm, and the width of a stem is preferably about 0.65 mm. The overall height of the pawl 48 and the width or thickness (or diameter if round) of the stem are preferably greater than minimum permissible values that will provide the pawl with enough strength and resistance to buckling during normal operation, but which allows the pawl to bend during the next subsequent actuation of the container and movement of the cap member after the final predetermined actuation of the container. The width of the head of the pawl allows it to function during the normal operation of the device, and further allows it to be nested with the ratchet wheel 82 after the pawl is bent when the cap member 20 and ratchet wheel 82 are at the bottom of subsequent strokes after the final predetermined actuation. Obviously, the various preferred dimensions described herein can be scaled up or down depending on the size of the overall indicator and force required to actuate the container, and the corresponding force of the return springs.

In an alternative embodiment, the base member includes a first lock member, configured as a post member extending upwardly from the bottom of the base member. The enlarged protrusion 91 defines a second lock member. In operation, the cap member is moved towards and away from the base member between a fully extended position, wherein the cap member is distal to the base member, and a bottom of the stroke position, wherein the cap member is proximate the base member, so as to rotate the indicator member as described above. During this operation, the first lock member is positioned below the protrusions of the indicator member so as to not interfere therewith. After the indicator member has made one complete rotation, which preferably correlates to an emptying of the container, the enlarged protrusion is rotated over the first lock member. In this position, the cap member cannot be moved toward the base member.

The immobility of the cap member provides visual and physical secondary indicia that the container should be replaced, and further prevents the mechanism from clicking or the indicator member from moving, thereby providing both a visual as well as an audible indication that the container should be replaced. It should be understood that the size and shape of the first and second lock members can be varied. For example, a post member may extend from the cap member so as to engage a stepped surface in the base member, which functions as a stop member.

In addition, it should be understood that, in one alternative embodiment, the pawl can be made sufficiently robust, for example by thickening the stem, such that when it is used with the stop member, the pawl engages the ratchet wheel and prevents the cap member from being moved toward the base member, rather than bending or buckling as described above with respect to another preferred embodiment. As such, the immobility of the cap member 20 relative to the base member 40, and the elimination of any clicking sound, provides further indicia to the user that the container should be replaced. It should also be understood that the lock member can extend from the cap member and engage a corresponding lock member on the base member.

Various indicating devices and components thereof are disclosed in U.S. Pat. Nos. 6,082,358, 6,336,453 and 6,328,037, all of which are hereby incorporated herein by reference. Although the indicating device has been described herein in connection with an aerosol container, it should be understood that it can be used with other dispensing devices which are actuated, with each actuation causing a movement of the drive member.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An indicating device comprising:
    a drive member rotatable about a first rotation axis, said drive member having a convex surface extending at least partially circumferentially about said first rotation axis, and a recess opening radially inwardly from said convex surface, said drive member comprising an engagement member; and
    a driven member rotatable about a second rotation axis, said driven member having a plurality of concave surfaces successively engaged by said convex surface of said drive member, wherein said driven member is immobilized non-rotatably about said second rotation axis by said successive engagement of said convex surface with said plurality of concave surfaces as said drive member rotates about said first rotation axis, and wherein said driven member further comprises a plurality of protrusions formed between adjacent ones of said plurality of concave surfaces, wherein said plurality of protrusions are successively received in said recess as said engagement member engages said driven member and rotates said driven member about said second rotation axis; and wherein said driven member comprises dispensing indicia.

2. The indicating device of claim 1 wherein said dispensing indicia are disposed on a surface of said driven member facing a direction substantially parallel to said second rotation axis.

3. The indicating device of claim 1 wherein said first and second rotation axes are substantially perpendicular.

4. The indicating device of claim 1 wherein said driven member comprises a plurality of teeth disposed at least partially circumferentially about said second rotation axis, wherein said engagement member successively engages at least one of said plurality of teeth while said plurality of protrusions are successively received in said recess.

5. The indicating device of claim 4 wherein said engagement member comprises a drive tooth extending radially from an axle defining said first rotation axis.

6. The indicating device of claim 5 wherein said drive tooth is axially displaced from a non-return member defining said convex surface and said recess.

7. The indicating device of claim 1 wherein said dispensing indicia comprises a first set of dispensing indicia, and wherein said drive member comprises a second set of dispensing indicia.

8. The indicating device of claim 1 wherein said drive member comprises a ratchet wheel, and further comprising a pawl successively engaging said ratchet wheel.

9. The indicating device of claim 8 further comprising a first housing component having a viewing window, wherein said dispensing indicia are visible through said viewing window, and a second housing component moveably coupled to said first housing component, wherein said drive member is secured to one of said first and second housing components, and said pawl member is secured to the other of said first and second housing components.

10. The indicating device of claim 9 wherein said first and second housing components are moveable relative to each other along an axis substantially perpendicular to said first rotation axis.

11. The indicating device of claim 9 further comprising a biasing component disposed between said first and second housing components.

12. A method for indicating the amount of substance that have been dispensed from or remain in a container, said method comprising:
    rotating a drive member about a first rotation axis, wherein said drive member has a convex surface extending at least partially circumferentially about said first rotation axis, and a recess opening radially inwardly from said convex surface;
    engaging a driven member with said drive member and thereby rotating said driven member an incremental amount about a second rotation axis, wherein said driven member has a plurality of concave surfaces and a plurality of protrusions formed between adjacent ones of said plurality of concave surfaces;
    disposing one of said plurality of protrusions in said recess as said driven member is engaged and rotated said incremental amount by said drive member;
    slidably engaging one of said concave surfaces of said driven member with said convex surface of said drive member and thereby preventing said driven member from rotating about said second rotation axis; and
    displaying dispensing indicia on said driven member.

13. The method of claim 12 wherein said displaying said dispensing indicia comprises displaying said dispensing indicia are on a surface of said driven member facing a direction substantially parallel to said second rotation axis.

14. The method of claim 12 wherein said first and second rotation axes are substantially perpendicular.

15. The method of claim 12 wherein said driven member comprises a plurality of teeth disposed at least partially circumferentially about said second rotation axis, and wherein said engaging said driven member with said drive member comprises successively engaging at least one of said plurality of teeth while said plurality of protrusions are successively received in said recess.

16. An indicating device comprising:
- an indicator member comprising dispensing indicia, wherein said indicator member is rotatable about a first rotation axis, and wherein said indicator member comprises a plurality of stop surfaces; and
- a stop member rotatable about a second rotation axis, wherein said stop member is selectively engaged with successive ones of said plurality of stop surfaces, wherein said indicator member is non-rotatable about said first rotation axis when said stop member is selectively engaged with one of said plurality of stop surfaces, wherein said stop member comprises a convex surface and wherein said plurality of stop surfaces each comprise a concave shaped to slidably mate with said convex surface, wherein said stop member is rotatable relative to said indicator member about said second axis while maintaining said indicator member in a stationary position non-rotatable about said first rotation axis.

17. The indicating device of claim 16 wherein said dispensing indicia are disposed on a surface of said indicator member facing a direction substantially parallel to said first rotation axis.

18. The indicating device of claim 16 wherein said first and second rotation axes are substantially perpendicular.

19. The indicating device of claim 16 further comprising a drive member coupled to said stop member, wherein said stop member is disengageable from said indicator member while said drive member is simultaneously engageable with said indicator member.

* * * * *

UNITED STATES PATENT AND TRADEMARK OFFICE
CERTIFICATE OF CORRECTION

| | | |
|---|---|---|
| PATENT NO. | : 8,082,873 B2 | Page 1 of 1 |
| APPLICATION NO. | : 12/434917 | |
| DATED | : December 27, 2011 | |
| INVENTOR(S) | : Michael Nuttall | |

It is certified that error appears in the above-identified patent and that said Letters Patent is hereby corrected as shown below:

In column 16, claim 16, line 1, before "shaped to slidably mate" insert --surface--.

Signed and Sealed this
Twentieth Day of March, 2012

David J. Kappos
*Director of the United States Patent and Trademark Office*